United States Patent
Rusai et al.

(10) Patent No.: US 9,968,636 B2
(45) Date of Patent: May 15, 2018

(54) PERITONEAL DIALYSIS FLUID COMPRISING A GSK-3 INHIBITOR

(71) Applicant: ZYTOPROTEC GMBH, Vienna (AT)

(72) Inventors: Krisztina Szilvia Rusai, Vienna (AT); Christoph Aufricht, Klosterneuburg-Weidling (AT)

(73) Assignee: ZYTOPROTEC GMBH, Vienna (AT)

(*) Notice: Subject to any disclaimer, the term of this patent is extended or adjusted under 35 U.S.C. 154(b) by 196 days.

(21) Appl. No.: 14/369,071

(22) PCT Filed: Dec. 19, 2012

(86) PCT No.: PCT/EP2012/076054
§ 371 (c)(1),
(2) Date: Jun. 26, 2014

(87) PCT Pub. No.: WO2013/098140
PCT Pub. Date: Jul. 4, 2013

(65) Prior Publication Data
US 2015/0004255 A1    Jan. 1, 2015

(30) Foreign Application Priority Data
Dec. 27, 2011 (EP) .................. 11195786

(51) Int. Cl.
| | |
|---|---|
| A61K 33/14 | (2006.01) |
| A61M 1/28 | (2006.01) |
| C01D 15/04 | (2006.01) |
| A61K 31/718 | (2006.01) |
| A61K 45/06 | (2006.01) |

(52) U.S. Cl.
CPC ............ *A61K 33/14* (2013.01); *A61K 31/718* (2013.01); *A61K 45/06* (2013.01); *A61M 1/287* (2013.01)

(58) Field of Classification Search
None
See application file for complete search history.

(56) References Cited

U.S. PATENT DOCUMENTS

2004/0121982 A1* 6/2004 Martis ................. A61K 31/718
514/58

FOREIGN PATENT DOCUMENTS

WO    WO 2008/106702 A1    9/2008

OTHER PUBLICATIONS

Perico, N., et al., Present and future drug treatments for chronic kidney diseases: evolving targets in renoprotection, Nature, 7 (2008) pp. 936-953.*
International Preliminary Report on Patentability for Application No. PCT/EP2012/076054 dated Jul. 1, 2014.
(Continued)

*Primary Examiner* — Bethany P Barham
*Assistant Examiner* — Dominic Lazaro
(74) *Attorney, Agent, or Firm* — Birch, Stewart, Kolasch & Birch, LLP (57) ABSTRACT

The present invention relates to a peritoneal dialysis fluid comprising a compound inhibiting glycogen synthase kinase (GSK)-3 activity, in particular (GSK)-3β activity, for use in the prevention of infectious and non-infectious peritoneal complications such as peritonitis, peritoneal membrane injury, damage and failure, barrier dysfunction and mesothelial cell detachment.

11 Claims, 4 Drawing Sheets

(56) References Cited

OTHER PUBLICATIONS

Abstract of Lal et al., "Lithium carbonate decreases ultrafiltration rates in an experimental model of PD", Int J Artif Organs., Nov. 1994, vol. 17, No. 11, pp. 573-575.

Abstract of Pugazhenthi et al., "Regulation of glycogen synthase activation in isolated hepatocytes", Mol Cell Biochem., 1995, vol. 149-150, pp. 95-101.

Amore et al., "Glucose degradation products increase apoptosis of human mesothelial cells," Nephrol Dial Transplant, 2003, vol. 18, pp. 677-688.

Bidmon et al., "Overexpression of HSP-72 confers cytoprotection in experimental peritoneal dialysis", Kidney International, 2004, vol. 66, No. 6, pp. 2300-2307.

Bijur et al., "Opposing actions of Phosphatidylinositol 3-Kinase and Glycogen Synthase Kinase-3beta in the Regulation of HSF-1 Activity", Journal of Neurochemistry, 2000, vol. 75, No. 6, pp. 2401-2408.

Chiu et al, "Molecular actions and therapeutic potential of lithium in preclinical and clinical studies of CNS disorders", Pharmacology and Therapeutics, 2010, vol. 128, No. 2, pp. 281-304.

Chu et al., "Transcriptional Activity of Heat Shock Factor 1 at 37 degrees C is Repressed through Phosphorylation on Two Distinct Serine Residues by Glycogen Synthase Kinase 3• and Protein Kinases C • and C•", The Journal of Biological Chemistry, 1998, vol. 273, pp. 18640-18646.

Chuang et al., "GSK-3 as a Target for Lithium-Induced Neuroprotection Against Excitotoxicity in Neuronal Cultures and Animal Models of Ischemic Stroke", Frontiers in Molecular Neuroscience, Aug. 9, 2011, vol. 4, Article. 15, pp. 1-12.

Cohen et al., "GSK3 Inhibitors: Development and Therapeutic Potential", Nature Reviews Drug Discovery, Jun. 2004, vol. 3, pp. 479-487.

Cuzzocrea et al., "Glycogen synthase kinase 3beta inhibition reduces the development of nonseptic shock induced by zymosan in mice", Shock, 2007, vol. 27, No. 1, pp. 97-107.

Davies et al., "Peritoneal solute transport predicts survival on CAPD independently of residual renal function", Nephrol Dial Transplant, 1998, vol. 13, pp. 962-968.

Flynn et al., "Intraperitoneal lithium administration for bipolar affective disorder in a patient on continuous ambulatory peritoneal dialysis", The International Journal of Artificial Organs, Mar. 1987, vol. 10, No. 2, pp. 105-107.

Gum et al., "Reduction of Protein Tyrosine Phosphatase 1B Increases Insulin-Dependent Signaling in ob/ob Mice", Diabetes, Jan. 2003, vol. 52, pp. 21-28.

Hatakeyama et al., "Upregulation by retinoic acid of transforming growth factor-beta-stimulated heat shock protein 27 induction in osteoblasts: involvement of mitogen-activated protein kinases", Biochimica et Biophysica Acta., 2002, vol. 1589, pp. 15-30.

He et al., "Glycogen Synthase Kinase 3• and Extracellular Signal-Regulated Kinase Inactivate Heat Shock Transcription Factor 1 by Facilitating the Disappearance of Transcriptionally Active Granules after Heat Shock", Mollecular and Cellular Biology, Nov. 1998, vol. 18, No. 11, pp. 6624-6633.

Hsiung et al., "Attenuated 5-HT1A receptor signaling in brains of suicide victims: involvement of adenylyl cyclase, phosphatidylinositol 3-kinase, Akt and mitogen-activated protein kinase", Journal of Neurochemistry, 2003, vol. 87, pp. 182-194.

Hu et al., "IFN-gamma Suppresses IL-10 Production and Synergizes with TLR2 by Regulating GSK3 and CREB/AP-1 Proteins", Immunity, May 2006, vol. 24, No. 5, pp. 563-574.

Jope et al., "Glycogen Synthase Kinase-3 (GSK3): Inflammation, Diseases, and Therapeutics," Neurochem Res., 2007, vol. 32, pp. 577-595.

Juhaszova et al., "Role of Glycogen Synthase Kinase-3beta in Cardioprotection", Circulation Research, 2009, vol. 104, pp. 1240-1252.

Kazemi et al., "O-Linked beta-N-acetylglucosamine (0-GlcNAc) Regulates Stress-induced Heat Shock Protein Expression in a GSK-3 beta-dependent Manner", Journal of Biological Chemistry, Dec. 2010, vol. 285, No. 50, pp. 39096-39107.

Kline et al., "Repression of the Heat Shock Factor 1 Transcriptional Activation Domain is Modulated by Constitutive Phosphorylation", Mollecular and Cellular Biology, 1997, vol. 17, No. 4, pp. 2107-2115.

Kratochwill et al., "Alanyl-Glutamine dipeptide restores the cytoprotective stress proteome of mesothelial cells exposed to peritoneal dialysis fluids", Nephrol Dial Transplant, Aug. 22, 2011, pp. 1-10.

Leung et al., "Glucose degradation products downregulate ZO-1 expression in human peritoneal mesothelial cells: the role of VEGF", Nephrol Dial Transplant, 2005, vol. 20, pp. 1336-1349.

Lin et al., "Advanced glycation end-product-inhibited cell proliferation and protein expression of beta-catenin and cyclin D1 are dependent on glycogen synthase kinase 3beta in LLC-PK1 cells", Archives of Biochemisty and Biophysics, 2008, vol. 477, pp. 27-32.

Mariappan et al., "Glycogen Synthase Kinase 3beta is a Novel Regulator of High Glucose- and High Insulin-induced Extracellular Matrix Protein Synthesis in Renal Proximal Tubular Epithelial Cells", The Journal of Biological Chemistry, 2008, vol. 283, pp 30566-30575.

Morisco et al., "Glycogen synthase kinase 3beta regulates GATA4 in cardiac myocytes", The Journal of Biological Chemistry, 2001, vol. 276, pp. 28586-28597.

Ren et al., "Postinsult treatment with lithium reduces brain damage and facilitates neurological recovery in a rat ischemia/reperfusion model," Proc Natl Acad Sci U S A., May 13, 2003, vol. 100, No. 10, pp. 6210-6215.

Riesenhuber et al., "Quercetin protects human mesothelial cells against exposure to peritoneal dialysis fluid", Pediatr Nephrol, Apr. 25, 2007, vol. 22, No. 8, pp. 1205-1208.

Ring et al., "Selective Glycogen Synthase Kinase 3 Inhibitors Potentiate Insulin Activation of Glucose Transport and Utilization In Vitro and In Vivo", Diabetes, Mar. 2003, vol. 52, pp. 588-595.

Rowe et al., "GSK-3 is a viable potential target for therapeutic intervention in bipolar disorder", Neurosci Biobehav Rev., 2007, vol. 31, No. 6, pp. 1-20.

Rowe et al., "Lithium neuroprotection: molecular mechanisms and clinical implications", Expert Review in Molecular Medicine, Oct. 8, 2004, vol. 6, Issue 21, pp. 1-18.

Ryves et al., "Glycogen Synthase Kinase-3 Inhibition by Lithium and Beryllium Suggests the Presence of Two Magnesium Binding Sites", Biochemical and Biophysical Research Communications, 2002, vol. 290, No. 3, pp. 967-972.

Ryves et al., "Lithium Inhibits Glycogen Synthase Kinase-3 by Competition for Magnesium", Biochemical and Biophysical Research Communication, 2001, vol. 280, pp. 720-725.

Takahashi-Yanaga et al., "GSK-3beta regulates cyclin D1 expression: a new target for chemotherapy", Cellular Signalling, 2008, vol. 20, pp. 581-589.

Vigh et al., "Can the stress protein response be controlled by 'membrane-lipid therapy'?", Trends in Biochemical Sciences, Jul. 31, 2007, vol. 32, No. 8, pp. 357-363.

Xu et al., "Enhancement of neuroprotection and heat shock protein induction by combined prostaglandin A1 and lithium in rodent models of focal ischemia", Brain Research, Aug. 2, 2006, vol. 1102, No. 1, pp. 154-162.

Xu et al., "Greater stress protein expression enhanced by combined prostaglandin A1 and lithium in a rat model of focal ischemia", Acta Pharmacol Sin, Aug. 2007, vol. 28, No. 8, pp. 1097-1104.

Zhou et al., "HSP72 inhibits Smad3 activation and nuclear translocation in renal epithelial-to-mesenchymal transition," J Am Soc Nephrol., 2010, vol. 21, pp. 598-609.

\* cited by examiner

PERITONEAL DIALYSIS FLUID COMPRISING A GSK-3 INHIBITOR

CROSS REFERENCE TO RELATED APPLICATIONS

This application is the National Phase of PCT International Application No. PCT/EP2012/076054, filed on Dec. 19, 2012, which claims priority under 35 U.S.C. 119(a) to Patent Application No. 11195786.6, filed in Europe on Dec. 27, 2011, all of which are hereby expressly incorporated by reference into the present application.

The present invention relates to a peritoneal dialysis fluid (in the following also referred to as "PDF").

Peritoneal dialysis (PD) is a safe and cost-effective renal replacement therapy also offering a better quality of life when compared to haemodialysis. Unfortunately, PD treatment frequently results in progressive decline of ultrafiltration capacity of the membrane usually associated with peritoneal histological changes and loss of peritoneal integrity (1).

Presently, more than two third of patients suffer from a PD related infectious or non-infectious complication (such as peritonitis, peritoneal membran function deterioration or technical failure) during their first two years on therapy.

Different kinds of fluids are available for PD. The difference between these fluids is the type of osmotic agents, their concentrations and the type of buffer and pH value in the PD fluid.

Standard fluids that still represent about 80% of all PD fluids in the clinical practice contain non-physiological high concentrations of glucose as their osmotic agent. Pathological changes in the peritoneum mainly result from the hyperosmolar high glucose concentration and also of low pH value (2). More complex and chronic injury is induced by glucose degradation products (GDPs), which are formed during heat sterilization of PD fluids (3). Novel and more bio-compatible glucose-based PD fluids have normal pH and low GDP content due to the usage of a more-chamber system; however, these fluids are highly expensive, therefore their clinical use is still limited in the global setting.

There are also alternative, non-glucose based PD fluids on the market such as icodextrin- or amino-acid-based PD fluids, however, their use is limited to a single exchange per day and their ultrafiltration capacity is not as good as that of glucose-based solutions. Moreover, they also have a lower pH value potentiating unfavourable cellular changes in the peritoneum.

Therefore, searching for strategies to reduce toxicity of PD fluids is still an actual field in experimental and clinical nephrology and has immense medical and socio-economic importance.

It has previously been demonstrated in a number of studies that HSPs have a significant impact on mesothelial cell survival in experimental PD since up-regulation of HSPs either by pharmacological or by plasmid-mediated way protected mesothelial cells from the toxic features of PD fluids (12,13,14).

Interestingly, however, incubation with standard glucose-based PD fluids resulted in a down-regulated HSP expression in mesothelial cells that causes a weakened cell defence mechanism.

WO 2008/106702 discloses a carbohydrate-based peritoneal dialysis fluid, containing a compound selected from the group consisting of glutamine, preferably L-glutamine,
a dipeptide capable of releasing glutamine, L-glutamine in free form, preferably selected from the group consisting of glutaminyl-glycine, glycinyl-glutamine, glutaminyl-alanine, alanyl-glutamine
an oligopeptide consisting of two to seven glutamine, preferably L-glutamine residues, and
mixtures thereof.

There is still a need for peritoneal dialysis fluids with which the occurrence of infectious and non-infectious peritoneal complications, such as peritonitis, peritoneal membrane injury, damage and failure, barrier dysfunction and mesothelial cell detachment can be prevented or at least inhibited. By way of preventing such infectious and non-infectious peritoneal complications, technical failure in a patient undergoing a PD-treatment can be inhibited. The term "technical failure" is well-known to the skilled artisan and means the need to terminate peritoneal dialysis, and to switch to alternate renal replacement therapies such as hemodialysis.

Therefore, it is an object of the present invention to provide a peritoneal dialysis fluid with which the occurrence of such infectious and non-infectious peritoneal complications can be prevented or inhibited.

In one aspect, the present invention relates to a peritoneal dialysis fluid comprising a compound inhibiting glycogen synthase kinase (GSK)-3 activity, in particular (GSK)-3β activity for use in the prevention of infectious and non-infectious peritoneal complications, such as peritonitis, peritoneal membrane injury, damage and failure, barrier dysfunction and mesothelial cell detachment.

In a further aspect, the present invention relates to a peritoneal dialysis fluid based on icodextrin, comprising a compound inhibiting glycogen synthase kinase (GSK)-3 activity, in particular (GSK)-3β activity.

In yet one further aspect, the present invention relates to a compound inhibiting glycogen synthase kinase (GSK)-3 activity, in particular (GSK)-3β activity for use in the prevention of infectious and non-infectious peritoneal complications, such as peritonitis, peritoneal membrane injury, damage and failure, barrier dysfunction and mesothelial cell detachment.

DETAILED DESCRIPTION OF THE INVENTION

The glycogen synthase kinase-3β (GSK-3β) is a serine-threonine protein kinase. GSK-3β itself is regulated and inhibited by phosphorylation at the serine-9 residue by different upstream kinases out of which Akt and the serum and glucocorticoid-regulated kinase-1 (SGK-1) have gained more attention (4). GSK-3β was originally identified as a key enzyme reacting to different levels of glucose and GDPs regulating thereby the glycogen synthesis (5,6). However, subsequent work demonstrated that GSK-3β has a central role in overall cell survival, cell cycle progression and migration.

Although GSK-3β was described approximately 30 years back, the interest in it as potential drug target became prominent only in the beginning of the present century as GSK-3β was discovered as a multi-faced kinase involved in several physiological and pathological processes. Studies reported that GSK-3β inhibition either by selective small molecule inhibitors or with lithium has protective properties in various disease models. GSK-3β inhibition was proved to improve insulin resistance in type II diabetes (23,24), to have beneficial effects in neurological disorders like Alzheimer's disease (25) and to reduce cardiac hypertrophy and ischemia (26).

Many GSK-3β targets are transcription factors (HSF-1, β-catenin, C-Jun, CREB) leading to altered stress reaction, increased apoptosis and changes in neurotransmission. GSK-3β is also capable of regulating cytoskeletal elements (7,8) that altogether render GSK-3β a central mediator in cellular signalling with an immense role in cell fate.

One of the major targets of GSK-3β is the heat shock factor-1 (HSF-1), the key inducer of the cell protective heat shock protein (HSP) expression (9,10). Under stress conditions, HSF-1 is activated in a multi-step way including hyperphosphorylation, translocation into the nucleus, binding of HS elements (HSE) followed by transcription of respective genes. HSF-1 is phosphorylated and thereby inhibited by GSK-3β (11) leading to reduced HSP levels. GSK-3β phosphorylates HSF-1 at the serine-303 residue regulating negatively its binding to the DNA and the HSF-1-dependent transcription which lead to suppressed HSP-72 production (21), on the other hand, GSK-3β inhibition increases the heat shock response contributing to improved cell defence As GSK-3β is strongly regulated by glucose and GDPs (15), the inventors of the present inventions have considered that it might be a relevant molecular player in PD-associated cellular signalling. However, a direct association between GSK-3β and PD has not yet been described.

It is hypothesized that an increase in the activity of the anti-survival GSK-3β—as possibly mediated by PD fluid exposure—inhibits the pro-survival HSF-1, the key regulator of HSP transcription during PD. Accordingly, blocking GSK-3β activity might result in enhanced activation of HSF-1, and thus, in higher HSP expression and in less cell toxicity.

It has now been found that GSK-3 inhibition, in particular GSK-3β inhibition decreased mesothelial cell injury and death rate in cells treated with PD fluids. Mesothelial cell protection was paralleled by higher HSF-1 activity and HSP-72 expression.

This effect is particularly pronounced with PD fluids selected from the group consisting of carbohydrate-based dialysis fluids and amino-acid based dialysis fluids. The effect is even more pronounced with carbohydrate-based peritoneal dialysis fluids with a pH-value of 7.3 or lower, preferably 7.0 or lower, most preferably 6.0 or lower.

Carbohydrate-based peritoneal dialysis fluids are especially those based on glucose or icodextrin. Most preferably, the peritoneal dialysis fluid is based on icodextrin.

Accordingly, a particularly preferred embodiment of the present invention is a peritoneal dialysis fluid based on icodextrin, comprising a compound inhibiting glycogen synthase kinase (GSK)-3 activity, in particular (GSK)-3β activity.

As mentioned above, a further aspect of the present invention relates to a compound inhibiting glycogen synthase kinase (GSK)-3 activity, in particular (GSK)-3β activity for use in the prevention of infectious and non-infectious peritoneal complications, such as peritonitis, peritoneal membrane injury, damage and failure, barrier dysfunction and mesothelial cell detachment caused by treatment with a peritoneal dialysis fluid.

The compound is preferably administered together with a peritoneal dialysis fluid in the course of a peritoneal dialysis treatment. The PD fluid is preferably selected from the PD fluids already discussed above.

The compound inhibiting glycogen synthase kinase (GSK)-3 activity, in particular (GSK)-3β activity is preferably selected from the group consisting of lithium, tideglusib, NP-103, GSK-3β Inhibitor I (TDZD-8, 4-Benzyl-2-methyl-1,2,4-thiadiazolidine-3,5-dione), GSK-3β Inhibitor II (2-Thio(3-iodobenzyl)-5-(1-pyridyl)-[1,3,4]-oxadiazole), GSK-3 Inhibitor IV (SB-216763, 3-(2,4-Dichlorophenyl)-4-(1-methyl-1H-indol-3-yl)-1H-pyrrole-2,5-dione), GSK-3 Inhibitor IX (BIO, (2'Z,3'E)-6-Bromoindirubin-3'-oxime), GSK-3β Inhibitor VI (2-Chloro-1-(4,5-dibromo-thiophen-2-yl)-ethanone), GSK-3β Inhibitor VII (2,4'-Dibromoacetophenone), GSK-3β Inhibitor VIII (AR A014418, N-(4-Methoxybenzyl)-N'-(5-nitro-1,3-thiazol-2-yl)urea), GSK-3 Inhibitor X (BIO-Acetoxime, (2'Z,3'E)-6-Bromoindirubin-3'-acetoxime), GSK-3β Inhibitor XI (3-(1-(3-Hydroxypropyl)-1H-pyrrolo[2,3-b]pyridin-3-yl]-4-pyrazin-2-yl-pyrrole-2,5-dione, 7AIPM), GSK-3 Inhibitor XIII (5-Methyl-1H-pyrazol-3-yl)-(2-phenylquinazolin-4-yl)amine), GSK-3β Inhibitor XII (TWS 119, 3-[[6-(3-Aminophenyl)-7H-pyrrolo[2,3-d]pyrimidin-4-yl]oxyphenol ditrifluoroacetate), GSK-3β Inhibitor XVIII (2-(Chloro-4-(4-thiophen-2-yl-pyrimidin-2-ylamino)-phenyl)-(4-methyl-piperazin-1-yl)-methanone), GSK-3β Inhibitor X (BIO-Acetoxime, (2'Z,3'E)-6-Bromoindirubin-3'-acetoxime), GSK-3β Inhibitor XI (3-(1-(3-Hydroxypropyl)-1H-pyrrolo[2,3-b]pyridin-3-yl]-4-pyrazin-2-yl-pyrrole-2,5-dione, 7AIPM), GSK-3β Inhibitor XIX (IM-12, $C_{22}H_{20}FN_3O_2$, indolylmaleimide-derivate), GSK-3 Inhibitor XVI (6-(2-(4-(2,4-Dichlorophenyl)-5-(4-methyl-1H-imidazol-2-yl)-pyrimidin-2-ylamino)ethylamino)-nicotinonitrile, CHIR99021), GSK-3 Inhibitor XVII (5-Benzylamino-3-oxo-2,3-dihydro-1,2,4-thiadiazole, TDZD-20), GSK-3 Inhibitor XXII, Compound A (6-Methyl-N-[3-[[3-(1-methylethoxy)propyl]carbamoyl]-1H-pyrazol-4-yl]pyridine-3-carboxamide), GSK-3β Inhibitor XXIII, 3F8 (5-Ethyl-7,8-dimethoxy-1H-pyrrolo[3,4-c]-isoquinoline-1,3-(2H)-dione), GSK-3β Peptide Inhibitor (L803, H-KEAPPAPPQSpP-NH$_2$), GSK-3β Peptide Inhibitor (L803-mts, Myr-N-GKEAPPAPPQSpP-NH$_2$), GF-109203X (2-[1-(3-Dimethylaminopropyl)indol-3-yl]-3-(indol-3-yl)maleimide) and pharmaceutically acceptable salts and mixtures thereof.

In a preferred embodiment, the compound inhibiting glycogen synthase kinase (GSK)-3 activity is a lithium salt, in particular lithium chloride or lithium carbonate. The concentration of the lithium salt in the dialysis fluid is preferably from 1 mM to 10 mM, most preferred 2 mM to 5 mM.

Lithium is a well-known GSK-3β inhibitor inhibiting GSK-3β by competition for magnesium (27). Lithium has been used for the treatment of bipolar mood disorders since the nineteen-fifties without knowing its specific mode of action at that time. In 1996, it was discovered to be a potent inhibitor of GSK-3β and evidence is growing that this may be one of the basis mechanisms for lithium's known and utilized mood stabilizing effects in bipolar disorder (16,17, 18,22). In addition to mood disorders, lithium is now in phase II clinical trial for the treatment of amyotrophic lateral sclerosis and for the treatment of intestinal graft versus host disease after donor stem cell transplant.

There is much less known about whether the downstream actions of GSK-3β inhibition by lithium directly involves the HSPs. However recently, the protective lithium effects were demonstrated to be associated with improved HSP levels in experimental models such as ischemic brain damage (30,31) and lithium's neuroprotective effects were also implicated to be directly due to induced HSF-1 activity (32,33).

Lithium has been added to glucose-based PD fluids in the clinical setting in order to treat bipolar symptoms of a patient on continuous ambulatory PD; however this application modality was then not introduced as routine administration (28). In this study, lithium was given in Dianeal® 2.5% solution in an end-dose of 0.9 mM in a 2 L bag and the solution was changed 3-times a day therefore yielding a continuous lithium exposure.

Later on, in an experimental rat PD model, lithium-carbonate was administered together with the glucose-based PD fluid to investigate its effects on acute ultrafiltration rate, results, however demonstrated the opposite effect that lithium decreased ultrafiltration rate (29). In this study, 5 mM Li was applied.

GSK-3β inhibition can also be achieved by alternative, specific pharmacological inhibitors as well (GSK-3 or GSK-3β inhibitors). There are several inhibitors available on the market. Some of these agents are currently under clinical investigations for therapy of special conditions, but none of them has yet been administered either in the PD solution or for the treatment of PD-caused decline of peritoneal function.

Out of the specific GSK-3 inhibitors, tideglusib ((Zentylor), non-ATP competitive inhibitor) is the only one already approved for clinical use. Zentylor obtained the approval from the FDA in 2010 for the treatment of progressive supranuclear palsy and is in phase II trial for the therapy of Alzheimer's disease. Other specific inhibitors are those named above.

In case of GSK-3 inhibitors other than lithium or lithium salts, suitable dosages of the respective inhibitor in the PD fluid can be easily determined by the skilled artisan.

EXAMPLES

Methods
Cell Culture

The human Met-5a cell line was purchased from American Type Culture Collection (ATCC, Rockville, Md.). All cells were cultured in M199 culture medium supplemented with L-glutamine (0.1 g/L), penicillin (100 U/mL), streptomycin (100 µg/mL), 10% fetal bovine serum (FBS) and propagated at 37° C. in a humidified air containing 5% $CO_2$ incubator. Standard chemicals were purchased from Sigma-Aldrich (St. Louis, Mo., USA) unless otherwise stated. Falcon™ tissue culture plastics (Becton Dickinson, Franklin Lakes, N.J., USA) were used for all cell culture procedures.
PDF Exposure For incubation with PDF, glucose-based, low pH (5.5) 3.86% fluid (Dianeal PD4 solution), icodextrin-based low pH (5.5) fluid (Extraneal); amino-acid-based fluid (pH 6.7) (Nutrineal), glucose-based, neutral pH, lactate/bicarbonate-buffered fluid (Physioneal) from Baxter AG, Vienna, Austria were used. Glucose-based, lactate-buffered, neutral pH solution (Balance) was obtained from Fresenius, Austria.

The control solution was M199 culture medium supplemented with L-glutamine (0.1 g/L), penicillin (100 U/mL), streptomycin (100 µg/mL) without fetal bovine serum.

PDF exposure model: confluent cultures on 12-well plates were exposed for the indicated times (30 min or 1 h) to the PD fluid solution or kept in parallel in control medium. For HSF-1 activity assay, cells were harvested and lysed immediately after exposure times, whereas for measurements of LDH and HSP-72, p-GSK-3β Western blot analysis, cells were allowed to recover by incubation with normal culture medium containing 10% FBS for 16 h.
LiCl Treatment Lithium-chloride (LiCl) was purchased from Sigma-Aldrich (St. Louis, Mo., USA), and was applied at a dose as indicated.
LDH Release For LDH analyses, 200 µL aliquots of supernatants were removed after the described experimental setup and kept on −20° C. until analyzed within 48 h. Measurements were performed in duplicates with Sigma TOX-7 LDH Kit according to the manufacturer's instructions. LDH efflux was normalized for protein content.
Neutral Red Uptake To assess cell viability by neutral red uptake, cells were seeded out to 96-well plates and exposed to different treatment protocols as described before. Neutral red uptake was measured using a standard reagent (Sigma-Aldrich, St. Louis, Mo., USA) according to the manufacturer's protocol.
Luciferase Assay To determine the specific binding of the heat shock factor-1 (HSF-1), a commercially available Luciferase Reporter Vector (LR0038, Panomics, Italy) containing the heat shock element [5'CTGGAATTTTCTAGACTG-GAATTTTCTAGACTGGAATTTTCTAGA3'] as well as an empty control vector were transfected into the MeT-5a cells. 24 h prior to transfection, MC were seeded onto 96-well cell culture plates and allowed to reach approximately 80-90% confluence on day of transfection. Before transfection per well 0.15 µl Fugene6 (Roche) transfection reagent and 0.1 µl HSE reporter vector or control vector were each diluted with 5 µl of normal growth medium without FCS and incubated for 5 min. The solutions were mixed incubated for 30 min. Of this mix 10 µl were added to each well incubated for 24 h at 5% $CO_2$ and 37° C. in a humidified atmosphere. Experimental exposures were carried out as described before and the cells were allowed to recover for 6 h in order to facilitate protein synthesis of the luciferase enzyme. Cells were washed and lysed using a commercially available buffer (E1531, Promega). The cell lysates were transferred to white flat bottom microplates (Nunc). The luciferase reagent (E1500, Promega) was added using an automatic pipette in 3 s intervals and the yielded signal was measured after 2 min using a luminometer plate reader (Flx800, BioTek).
Western Blot Analysis For western blotting, protein content is determined by the Bradford assay (Biorad, Vienna, Austria) and equal amounts of protein samples (2 µg/lane) are separated by standard SDS-PAGE using a Pharmacia Multiphore II unit. Size-fractionated proteins are then transferred to PVDF membranes by semi-dry transfer in a Pharmacia Multiphore II Novablot unit. Membranes are blocked in 5% dry milk in TBS-Tween (10 mM Tris, 150 mM NaCl, 0.05% Tween 20, pH 7.4). Membranes are incubated with the respective primary antibody (HSP-72, p-GSK-3β) for 16 h. Detection is accomplished by incubation with secondary, peroxidase-coupled antibodies (anti-mouse or anti-rabbit IgG, both Dako Cytomation, Calif., USA) and enhanced chemiluminescence (ECL) using the ECL western blotting analysis system (Renaissance, NEN-Life Science Products, Boston, Mass., USA).

Data Analysis

All statistical analyses were performed using Sigmaplot 11.0 software (Systat Software GmbH, Erkrath, Germany). Values from different groups were compared using t-tests or ANOVA where appropriate. In case of ANOVA, Tukey's HSD was used as post-hoc test. A P-value of <0.05 was considered to be significant. The results are presented as means±SEM.

Results

Incubation with Conventional PD Fluid Induces Mesothelial Cell Injury and Death

Incubation of mesothelial cells with glucose-based low pH, lactate-buffered peritoneal dialysis fluid (PDF, Dianeal) and in low pH icodextrin-based PDF (Extraneal) resulted in severe cell injury reflected by shrinkage, detachment and in part, by fragmentation of cells demonstrated by light microscopy and vital-dead staining (data not shown).

This was paralleled by high LDH release (data not shown), by significantly reduced cell viability and by high rate of dead cells.

Incubation with PD Fluids Increases the Level of Activated GSK-3β

PDF incubation decreased the level of the inactive, Ser-9 phosphorylated GSK-3β (p-GSK-3β) analysed by immunofluorescent staining (data not shown) and by Western blotting (FIG. 1), whereas the level of total GSK-3β remained unchanged (FIG. 1) leading therefore to a higher net level of kinase-active GSK-3β compared to control cells.

The cellular expression and in particular, localisation of p-GSK-3β was analyzed by immunofluorescent staining. After incubation with different PD fluids, there was an overall lower expression of the p-GSK-3β especially in glucose-based, low pH PDF and icodextrin-based fluid treated cells, paralleled by a marked condensation around the nucleus (data not shown). However, also in the other treatment groups (lactate-buffered, lactate/bicarbonate buffered and aminoacid based PD fluids), a decrease and condensation when compared to control cells was observed.

Figure 1:
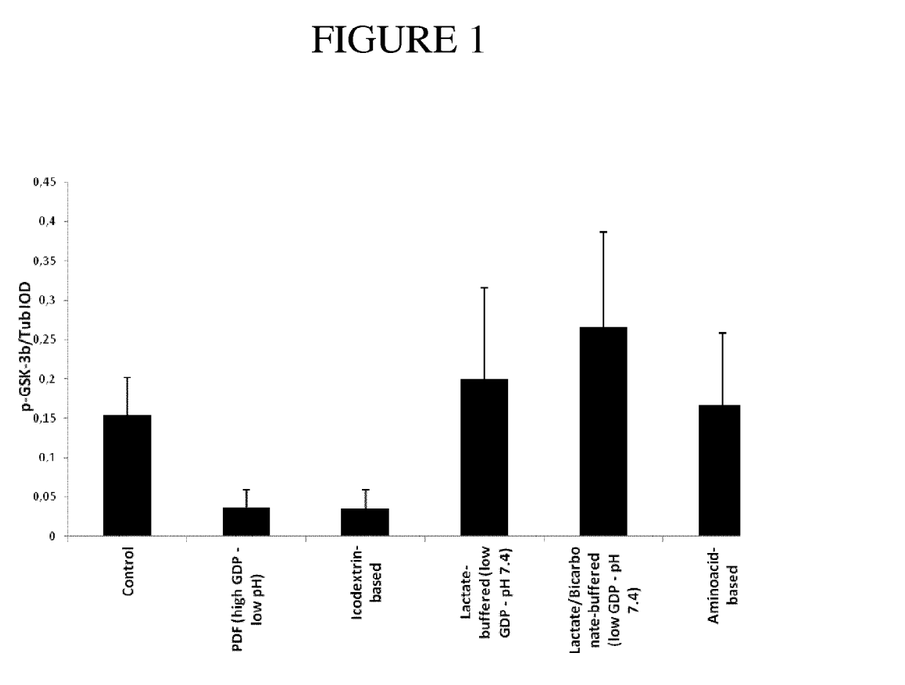
FIG. 1: p-GSK-3β expression in mesothelial cells treated with different commercially available PD fluids with different osmotic agents and toxic properties

The impact of different commercially available PD fluids on Ser-9 p-GSK-3β showed that low pH icodextrin-based PD fluids (Extraneal) had a similar effect to that of the glucose-based low pH solution, i.e. significantly lower expression of p-GSK-3β. The effect is less pronounced in normal pH glucose-based (lactate- or lactate/bicarbonate-buffered; Balance and Physioneal, respectively) PD fluids and amino-acid-based PD fluid (Nutrineal) with a moderate acidic pH (pH 6.7) (FIG. 1). These results are in line with previous observations on glucose and GDPs (19,20). These studies reported that high glucose decreased (19), whereas the end-products of GDPs up-regulated GSK-3β activity (20).

Description of FIG. 1: p-GSK-3β expression in mesothelial cells treated with different commercially available PD fluids with different osmotic agents and toxic properties. Control cells were treated with normal cell culture medium, PDF treated cells were treated with glucose-based, low pH PD fluid with high GDP content (PDF, Dianeal). Icodextrin-based PD fluid (Extraneal), lactate-buffered, low GDP, pH 7.4 (Balance), lactate/bicarbonate-buffered, low GDP, pH 7.4 (Physioneal), Amino-acid based (Nutrineal) PD fluid. (1 h exposure without recovery). *P<0.01 vs. Control.

Figure 2:
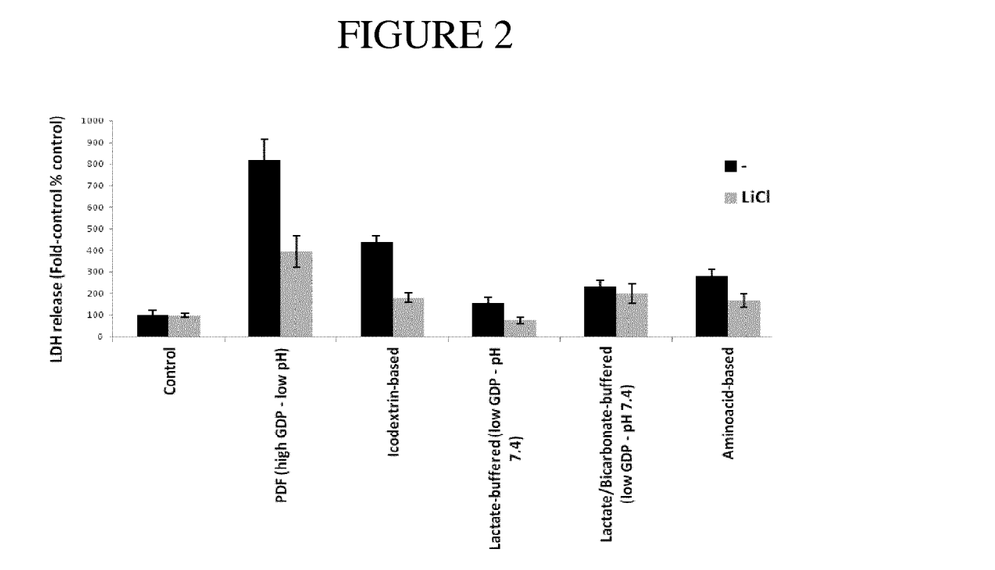
FIG. 2: LDH release in mesothelial cells treated with different commercially available PD fluids with different osmotic agents and toxic properties.

Lithium Inhibits GSK-3β, Leading to Reduced Cell Injury and Death in Mesothelial Cells after PD Fluid Incubation Glucose-based low pH, high GDP-containing and low pH icodextrin-based PD fluids caused a marked LDH elevation, paralleled by significant reduction in cell viability compared to controls (FIG. 2). Glucose-based normal pH and amino-acid-based PD fluids caused a more moderate significant LDH release (FIG. 2) that was not associated with significant cell death (data not shown).

In these PD fluid exposure systems, inhibition of GSK-3β activity with addition of 10 mM LiCl, reduced cell injury after treatment with all PD fluids observed, as reflected by attenuated LDH release (FIG. 2). The most prominent protection was observed after incubation with low pH glucose-based and icodextrin-based solutions (FIG. 2).

Therefore, protective effects of LiCl in these exposure systems were further investigated using live-dead staining and measurement of viable cells by neutral red uptake. Treatment with LiCl resulted in preserved cell structure (data not shown), in reduced rate of dead cells (data not shown) and in increased number of viable cells (FIG. 3) after incubation either with low pH glucose-based or icodextrin-based PD fluids.

Explanation of FIG. 2: LDH release in mesothelial cells treated with different commercially available PD fluids with different osmotic agents and toxic properties. Control cells were treated with normal cell culture medium, PDF treated cells were treated with glucose-based, low pH PD fluid with high GDP content (Dianeal). Icodextrin-based PD fluid (Extraneal), lactate-buffered, low GDP, pH 7.4 (Balance), lactate/bicarbonate-buffered, low GDP, pH 7.4 (Physioneal) PD fluid, Amino-acid-based (Nutrineal) PD fluid. LiCl was applied at a dose of 10 mM. #P<0.05 vs. Control, *P<0.01 vs. no LiCl treatment. (1 h exposure, 16 h recovery)

Figure 3:
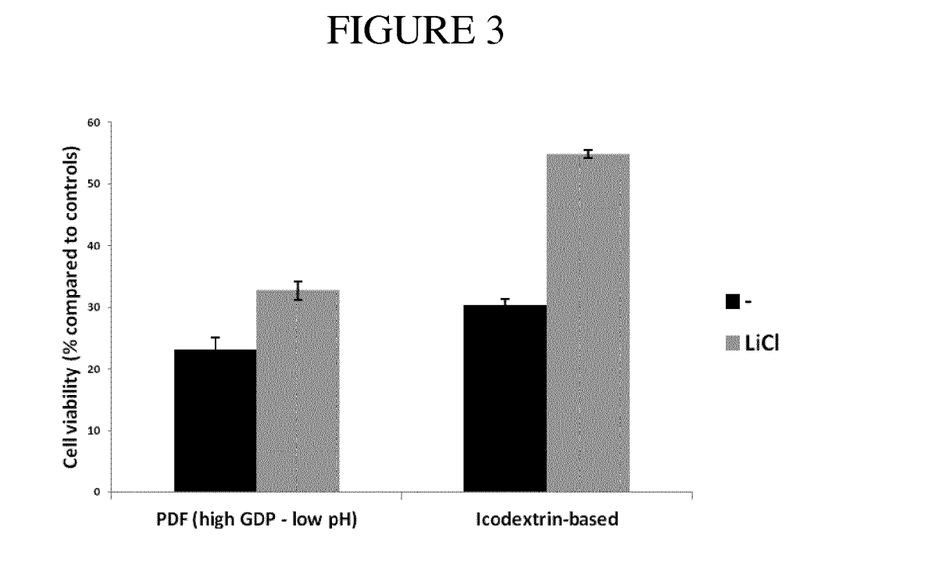
FIG. 3: Cell viability assessed by neutral red uptake in % compared to control cells.

Explanation of FIG. 3: Cell viability assessed by neutral red uptake in % compared to control cells. Cells were treated either with PDF (glucose-based, low pH PD fluid with high GDP content (Dianeal)) or with icodextrin-based PD fluid with low pH (Extraneal). LiCl was applied at a dose of 10 mM. #P<0.01 vs. Control, *P<0.01 vs. no LiCl treatment. (1 h exposure, 16 h recovery). Control cells were treated with normal cell culture medium.

LiCl Leads to Higher HSF-1 Activity

Figure 4:
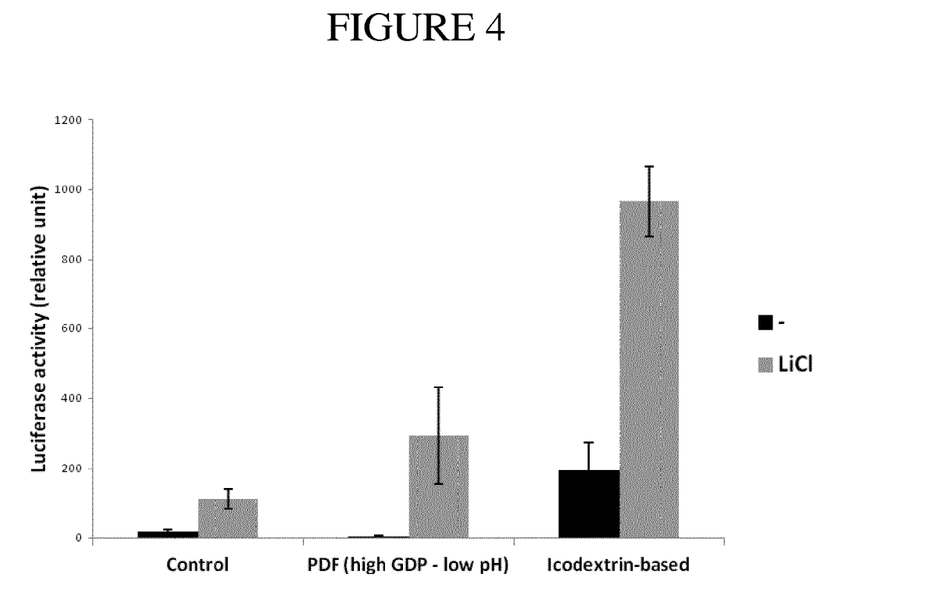
FIG. 4: Heat shock factor-1 activity assessed by Luciferase assay.

Luciferase assay showed that LiCl treatment significantly increased HSF-1 transcriptional activity in control cells and both after incubation with glucose-based low pH, high GDP-containing and low pH icodextrin-based PD fluids (FIG. 4).

Explanation of FIG. 4: Heat shock factor-1 activity by Luciferase assay. Control cells were treated with normal cell culture medium, PDF treated cells were treated with glucose-based, low pH PD fluid with high GDP content (Dianeal). Icodextrin-based PD fluid with low pH (Extraneal). LiCl was applied at a dose of 10 mM. (30 min exposure, 6 h recovery), #P<0.01 vs. Control, *P<0.01 vs. no LiCl treatment, respectively.

LiCl Treatment Results in Higher HSP-72 Expression

HSP-72 was assessed in cells treated with glucose-based, low pH PD fluid with high GDP content or with icodextrin-based PD fluid with or without LiCl administration after 30 min or 1 h incubation.

Figure 5:
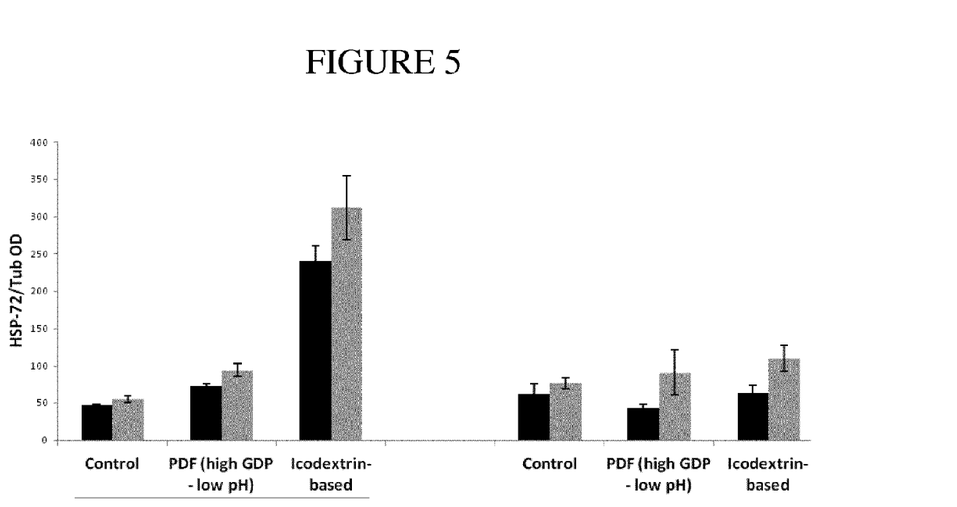
FIG. 5: Heat shock protein-72 (HSP-72) expression assessed by Western blot.

HSP-72 expression slightly increased after 30 min incubation and significantly decreased after 1 h incubation with glucose-based low pH, high GDP-containing fluid compared to control cells (FIG. 5). Expression of HSP-72 increased after 30 min incubation, but was unchanged after 1 h incubation with icodextrin-based PD fluid compared to controls (FIG. 5). Treatment with LiCl significantly increased the level of HSP-72 in each incubation setting when compared to the respective untreated cells.

Explanation of FIG. 5: Heat shock protein-72 (HSP-72) expression assessed by Western blot. Control cells were treated with normal cell culture medium, PDF treated cells were treated with glucose-based, low pH PD fluid with high GDP content (Dianeal). Icodextrin-based PD fluid with low pH (Extraneal). LiCl was applied at a dose of 10 mM. (30 min—left diagram—or 1 h exposure—right diagram, 16 h recovery). *P<0.05 vs. Control, % P<0.001 vs. Control, & P<0.05 vs. no LiCl treatment, respectively.

Dose Curve Analysis of LiCl Administration

In order to examine in which concentrations lithium effectively ameliorates mesothelial cell injury, a dose curve was analyzed during incubations with either low pH glucose-based (PDF) or icodextrin-based fluids. A dose of 1 mM, 2 mM, 5 mM and 10 mM LiCl was examined.

Figure 6:
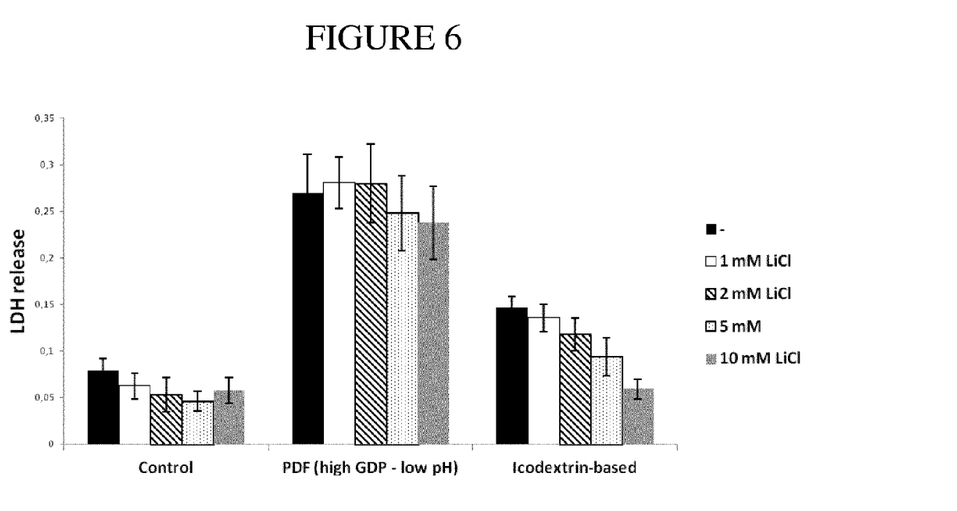
FIG. 6: LDH release into the supernatant.

In low pH glucose-based (PDF) fluid, LiCl at a dose from 1 mM to 5 mM did not alter the release of LDH into the supernatant (FIG. 6), but as detected previously, 10 mM LiCl significantly reduced LDH release when compared to controls (FIG. 6). During incubation with the icodextrin-based fluid, there was a dose-dependent LDH response curve: 1 mM LiCl did not change significantly, whereas 2 mM LiCl already decreased LDH levels and the decrease was even more significant administering 5 mM and 10 mM LiCl (FIG. 6).

Explanation of FIG. 6: LDH release into the supernatant. Control cells were treated with normal cell culture medium, PDF treated cells were treated with glucose-based, low pH PD fluid with high GDP content (Dianeal). Icodextrin-based PD fluid with low pH (Extraneal). LiCl was applied at a dose of 1 mM, 2 mM, 5 mM or 10 mM. (30 min exposure, 6 h recovery). #P<0.001 vs. Control, *P<0.05 vs. no LiCl treatment, respectively.

Figure 7:
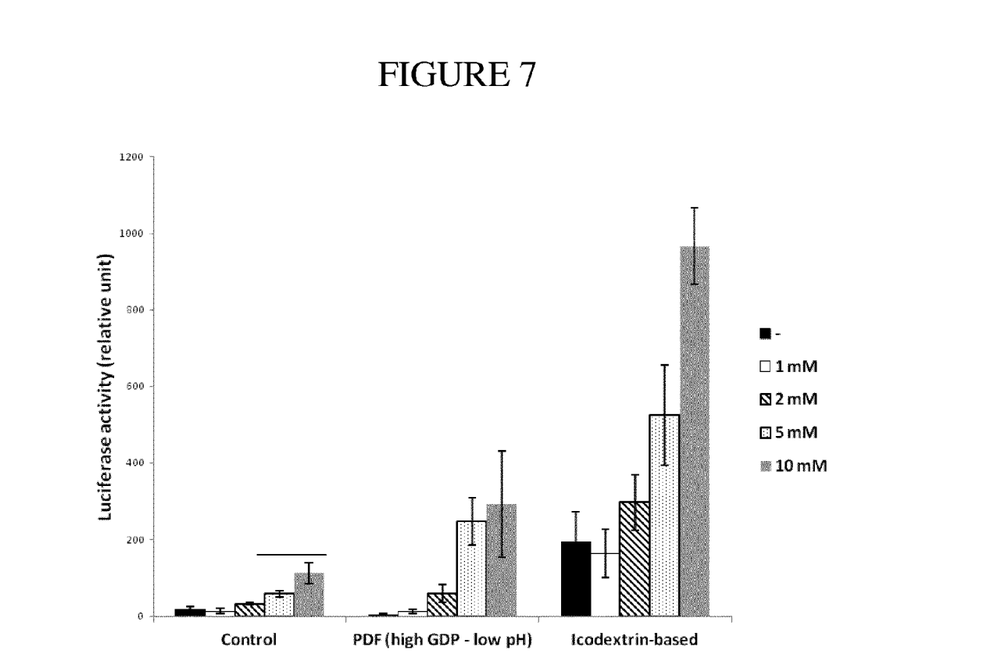
FIG. 7: Heat shock factor (HSF-1) translational activity assessed by Luciferase assay.

HSF-1 activity assessed by Luciferase assay showed that in cells incubated with either low pH glucose-based or with icodextrin-based PDF, there was a dose-dependent upregulation of HSF-1 activity compared to the respective control cells (FIG. 7).

Explanation of FIG. 7: Heat shock factor (HSF-1) translational activity assessed by Luciferase assay. Control cells were treated with normal cell culture medium, PDF treated cells were treated with glucose-based, low pH PD fluid with high GDP content (Dianeal). Icodextrin-based PD fluid with low pH (Extraneal). LiCl was applied at a dose of 1 mM, 2 mM, 5 mM or 10 mM. (30 min exposure, 6 h recovery). #P<0.01 vs. Control, *P<0.01 vs. no LiCl treatment, respectively.

Figure 8:
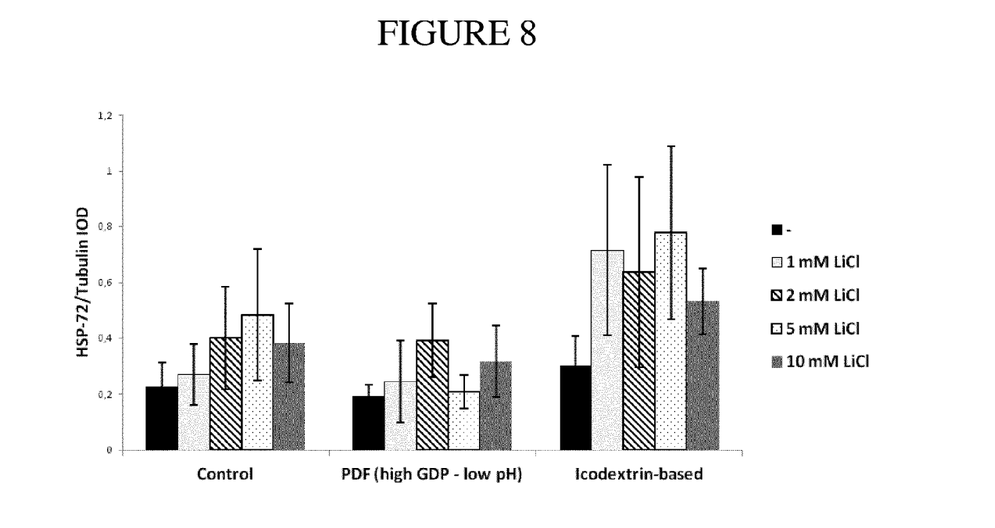
FIG. 8: Heat shock protein-72 (HSP-72) expression assessed by Western blot.

In cells incubated with glucose-based low pH PDF, HSP-72 expression increased only after administration of either 2 mM or 10 mM LiCl when compared to untreated cells (FIG. 8). On the other hand, after incubation with icodextrin-based PD fluid, all the applied LiCl doses increased the HSP-72 protein expression (FIG. 8).

Explanation of FIG. 8: Heat shock protein-72 (HSP-72) expression assessed by Western blot. Control cells were treated with normal cell culture medium, PDF treated cells were treated with glucose-based, low pH PD fluid with high GDP content (Dianeal). Icodextrin-based PD fluid with low pH (Extraneal). LiCl was applied at a dose of 1 mM, 2 mM, 5 mM or 10 mM. (30 min exposure, 16 h recovery). #P<0.05 vs. Control, *P<0.05 vs. no LiCl treatment, respectively.

Summary:

In the present study, lithium-chloride (LiCl) decreased LDH release, reduced cell death rate and improved cell viability. The effect is most pronounced with mesothelial cells treated with glucose-based low pH and icodextrin-based PD fluids, the commercially available PD fluids with the most significant effects on GSK-3β activation.

LITERATURE (1) Davies S J, Phillips L, Russell G I. Peritoneal solute transport predicts survival on CAPD independently of residual renal function. Nephrol Dial Transplant. 1998; 13: 962-68.

(2) Leung J C, Chan L Y, Li F F, Tang S C, Chan K W, Chan T M et al. Glucose degradation products downregulate ZO-1 expression in human peritoneal mesothelial cells: the role of VEGF. Nephrol Dial Transplant. 2005; 20: 1336-49.

(3) Amore A, Cappelli G, Cirina P, Conti G, Gambaruto C, Silvestro L et al. Glucose degradation products increase apoptosis of human mesothelial cells. Nephrol Dial Transplant. 2003; 18: 677-88.

(4) Juhaszova M, Zorov D B, Yaniv Y, Nuss H B, Wang S, Sollott S J. Role of glycogen synthase kinase-3beta in cardioprotection. Circ Res. 2009; 104: 1240-52. Review.

(5) Pugazhenthi S, Khandelwal R L. Regulation of glycogen synthase activation in isolated hepatocytes. Mol Cell Biochem. 1995; 149-150:95-101.

(6) Cuzzocrea S, Di Paola R, Mazzon E, Crisafulli C, Genovese T, Muia C et al. Glycogen synthase kinase 3beta inhibition reduces the development of nonseptic shock induced by zymosan in mice. Shock. 2007; 27: 97-107.

(7) Hatakeyama D, Kozawa O, Niwa M, Matsuno H, Ito H, Kato K, Tatematsu N, Shibata T, Uematsu T. Upregulation by retinoic acid of transforming growth factor-beta-stimulated heat shock protein 27 induction in osteoblasts: involvement of mitogen-activated protein kinases. Biochim Biophys Acta. 2002; 1589: 15-30.

(8) Takahashi-Yanaga F, Sasaguri T.GSK-3beta regulates cyclin D1 expression: a new target for chemotherapy. Cell Signal. 2008; 20: 581-9.

(9) Kline M P, Morimoto R I. Repression of the heat shock factor 1 transcriptional activation domain is modulated by constitutive phosphorylation. Mol Cell Biol. 1997; 17: 2107-15.

(10) He, Y. H. Meng and N. F. Mivechi. Glycogen synthase kinase 3β and extracellular signal-regulated kinase inactivate heat shock transcription factor 1 by facilitating the disappearance of transcriptionally active granules after heat shock. Mol. Cell Biol. 1998; 18: 6624-6633.

(11) Chu, R. Zhong, F. Soncin, M. A. Stevenson and S. K. Calderwood, Transcriptional activity of heat shock factor 1 at 37 degrees C. is repressed through phosphorylation on two distinct serine residues by glycogen synthase kinase 3 and protein kinases Cα and Cζ. J. Biol. Chem. 1998; 273: 18640-18646.

(12) Riesenhuber A, Kasper D C, Vargha R, Endemann M, Aufricht C. Quercetin protects human mesothelial cells against exposure to peritoneal dialysis fluid. Pediatr Nephrol. 2007 August; 22(8):1205-8.

(13) Bidmon B, Endemann M, Arbeiter K, Ruffingshofer D, Regele H, Herkner K, Eickelberg O, Aufricht C. Overexpression of HSP-72 confers cytoprotection in experimental peritoneal dialysis. Kidney Int. 2004 December; 66(6): 2300-7.

(14) Kratochwill K, Boehm M, Herzog R, Lichtenauer A, Salzer E, Lechner M, Kuster L, Bergmeister K, Rizzi A, Mayer B, Aufricht C. Alanyl-Glutamine dipeptide restores the cytoprotective stress proteome of mesothelial cells exposed to peritoneal dialysis fluids. Nephrol Dial Transplant in press.

(15) Mariappan M M, Shetty M, Sataranatarajan K, Choudhury G G, Kasinath B S. Glycogen synthase kinase 3beta is a novel regulator of high glucose- and high insulin-induced extracellular matrix protein synthesis in renal proximal tubular epithelial cells. J Biol Chem. 2008; 283: 30566-75.

(16) Cohen P, Goedert M. GSK3 inhibitors: development and therapeutic potential. Nat Rev Drug Discov. 2004; 3:479-87.

(17) Jope R S, Yuskaitis C J, Beurel E. Glycogen synthase kinase-3 (GSK3): inflammation, diseases, and therapeutics. Neurochem Res. 2007; 32: 577-95.

(18) Ryves W J, Harwood A J. Lithium inhibits glycogen synthase kinase-3 by competition for magnesium. Biochem Biophys Res Commun 2001; 280: 720-725.

(19) Zhou Y, Mao H, Li S, Cao S, Li Z, Zhuang S et al. HSP72 inhibits Smad3 activation and nuclear translocation in renal epithelial-to-mesenchymal transition. J Am Soc Nephrol. 2010; 21: 598-609.

(20) Lin K H, Guh J Y, Mo J F, Chiou S J, Hwang C C, Chuang L Y. Advanced glycation end-product-inhibited cell proliferation and protein expression of beta-catenin and cyclin D1 are dependent on glycogen synthase kinase 3beta in LLC-PK1 cells. Arch Biochem Biophys. 2008; 477: 27-32.

(21) Rowe M K, Wiest C, Chuang D M. GSK-3 is a viable potential target for therapeutic intervention in bipolar disorder. Neurosci Biobehav Rev. 2007; 31(6):920-31.

(22) Chuang D M, Wang Z, Chiu C T. GSK-3 as a Target for Lithium-Induced Neuroprotection Against Excitotoxicity in Neuronal Cultures and Animal Models of Ischemic Stroke. Front Mol Neurosci. 2011; 4:15. Epub 2011 Aug. 9.

(23) Gum R J, Gaede L L, Koterski S L, Heindel M, Clampit J E, Zinker B A et al. Reduction of protein tyrosine phosphatase 1B increases insulin-dependent signaling in ob/ob mice. Diabetes 2003; 52: 21-28.

(24) Ring D B, Johnson K W, Henriksen E J, Nuss J M, Goff D, Kinnick T R et al. Selective glycogen synthase kinase 3 inhibitors potentiate insulin activation of glucose transport and utilization in vitroand in vivo. Diabetes 2003; 52: 588-595.

(25) Hsiung S C, Adlersberg M, Arango V, Mann J J, Tamir H, Liu K P. Attenuated 5-HT1A receptor signaling in brains of suicide victims: involvement of adenylyl cyclase, phosphatidylinositol 3-kinase, Akt and mitogen-activated protein kinase. J Neurochem 2003; 87: 182-194.

(26) Morisco C, Seta K, Hardt S E, Lee Y, Vatner S F, Sadoshima J. Glycogen synthase kinase 3beta regulates GATA4 in cardiac myocytes. J Biol Chem 2001; 276: 28586-28597.

(27) Ryves W J, Dajani R, Pearl L, Harwood A J. Glycogen synthase kinase-3 inhibition by lithium and beryllium suggests the presence of two magnesium binding sites. Biochem Biophys Res Commun. 2002 Jan. 25; 290(3):967-72.

(28) Flynn C T, Chandran P K, Taylor M J, Shadur C A. Intraperitoneal lithium administration for bipolar affective disorder in a patient on continuous ambulatory peritoneal dialysis. Int J Artif Organs. 1987 March; 10(2):105-7.

(29) Lal S M, Moore H L, Groshong T D, Nolph K D. Lithium carbonate decreases ultrafiltration rates in an experimental model of PD. Int J Artif Organs. 1994 November; 17(11):573-5.

(30) Xu X H, Zhang H L, Han R, Gu Z L, Qin Z H. Enhancement of neuroprotection and heat shock protein induction by combined prostaglandin Al and lithium in rodent models of focal ischemia. Brain Res. 2006 Aug. 2; 1102(1):154-62.

(31) Xu X H, Hua Y N, Zhang H L, Wu J C, Miao Y Z, Han R, Gu Z L, Qin Z H. Greater stress protein expression enhanced by combined prostaglandin Al and lithium in a rat model of focal ischemia. Laboratory of Aging and Nervous Disease, Soochow University School of Medicine, Suzhou, China.

(32) Ren M, Senatorov V V, Chen R W, Chuang D M. Postinsult treatment with lithium reduces brain damage and facilitates neurological recovery in a rat ischemia/reperfusion model. Proc Natl Acad Sci USA. 2003 May 13; 100(10):6210-5.

(33) Rowe M K, Chuang D M. Lithium neuroprotection: molecular mechanisms and clinical implications. Expert Rev Mol Med. 2004 Oct. 18; 6(21):1-18.

The invention claimed is:

1. Peritoneal dialysis fluid based on icodextrin, comprising icodextrin and a compound inhibiting glycogen synthase kinase (GSK)-3 activity, wherein the compound inhibiting glycogen synthase kinase (GSK)-3 activity is lithium or a pharmaceutically acceptable salt thereof.

2. Peritoneal dialysis fluid according to claim 1, characterized in that the compound inhibiting glycogen synthase kinase (GSK)-3 activity is a lithium salt.

3. Peritoneal dialysis fluid according to claim 2, characterized in that the concentration of the lithium salt in the dialysis fluid is from 1 mM to 10 mM.

4. Peritoneal dialysis fluid according to claim 1, wherein the glycogen synthase kinase (GSK)-3 activity is a (GSK)-3 β activity.

5. Peritoneal dialysis fluid according to claim 2, wherein the lithium salt is lithium chloride or lithium carbonate.

6. Peritoneal dialysis fluid according to claim 3, wherein the concentration of the lithium salt in the dialysis fluid is from 2 mM to 5 mM.

7. Peritoneal dialysis fluid according to claim 1, wherein the peritoneal dialysis fluid has a pH value and the pH value of the peritoneal dialysis fluid is 7.3 or lower.

8. Peritoneal dialysis fluid according to claim 7, wherein the pH value of the peritoneal dialysis fluid is 7.0 or lower.

9. Peritoneal dialysis fluid according to claim 7, wherein the pH value of the peritoneal dialysis fluid is 6.0 or lower.

10. A method for the treatment of infectious and noninfectious peritoneal complications, the method comprising the step of:
    treating a patient by peritoneal dialysis by administrating the peritoneal dialysis fluid according to claim 1.

11. The method according to claim 10, wherein the infectious and noninfectious peritoneal complications are selected from the group consisting of peritonitis, peritoneal membrane injury, peritoneal membrane damage, peritoneal membrane failure, barrier dysfunction and mesothelial cell detachment.

* * * * *

SEQUENCE LISTING

```
<160> NUMBER OF SEQ ID NOS: 3

<210> SEQ ID NO 1
<211> LENGTH: 11
<212> TYPE: PRT
<213> ORGANISM: Artificial
<220> FEATURE:
<223> OTHER INFORMATION: GSK-3beta Peptide Inhibitor L803
<220> FEATURE:
<221> NAME/KEY: MOD_RES
<222> LOCATION: (10)..(10)
<223> OTHER INFORMATION: X = Ser(PO3H)

<400> SEQUENCE: 1

Lys Glu Ala Pro Pro Ala Pro Pro Gln Xaa Pro
1               5                   10

<210> SEQ ID NO 2
<211> LENGTH: 12
<212> TYPE: PRT
<213> ORGANISM: Artificial
```

```
<220> FEATURE:
<223> OTHER INFORMATION: GSK-3beta Peptide Inhibitor L803-mts
<220> FEATURE:
<221> NAME/KEY: LIPID
<222> LOCATION: (1)..(1)
<223> OTHER INFORMATION: MYRISTATE
<220> FEATURE:
<221> NAME/KEY: MOD_RES
<222> LOCATION: (11)..(11)
<223> OTHER INFORMATION: X = Ser(PO3H)

<400> SEQUENCE: 2

Gly Lys Glu Ala Pro Pro Ala Pro Pro Gln Xaa Pro
1               5                   10

<210> SEQ ID NO 3
<211> LENGTH: 45
<212> TYPE: DNA
<213> ORGANISM: Artificial
<220> FEATURE:
<223> OTHER INFORMATION: heat shock element of Luciferase Reporter
      Vector LR0038

<400> SEQUENCE: 3
ctggaatttt ctagactgga attttctaga ctggaatttt ctaga            45
```